US010618873B2

(12) United States Patent
Dehn et al.

(10) Patent No.: US 10,618,873 B2
(45) Date of Patent: Apr. 14, 2020

(54) METHOD FOR PRODUCING C4-C15 LACTAMS

(71) Applicant: BASF SE, Ludwigshafen am Rhein (DE)

(72) Inventors: Richard Dehn, Ludwigshafen (DE); Ahmad Dehestani, Walnut Creek, CA (US); Klemens Massonne, Bad Dürkheim (DE); Steffen Waglöhner, Nussloch (DE); Joaquim Henrique Teles, Waldsee (DE); Thomas Schaub, Neustadt (DE); Till Christian Brüggemann, Ludwigshafen (DE); Carlos Tellaeche Herranz, Heidelberg (DE); Oliver Trapp, Dossenheim (DE); Jedrzej Wysocki, Heidelberg (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/073,941

(22) PCT Filed: Jan. 30, 2017

(86) PCT No.: PCT/EP2017/051887
§ 371 (c)(1),
(2) Date: Jul. 30, 2018

(87) PCT Pub. No.: WO2017/133995
PCT Pub. Date: Aug. 10, 2017

(65) Prior Publication Data
US 2019/0040005 A1 Feb. 7, 2019

(30) Foreign Application Priority Data

Feb. 1, 2016 (EP) ..................................... 16153603

(51) Int. Cl.
*C07D 201/10* (2006.01)
*C07B 43/02* (2006.01)
*C07B 43/06* (2006.01)
*C07D 201/02* (2006.01)
*B01J 29/06* (2006.01)

(52) U.S. Cl.
CPC ............ *C07D 201/10* (2013.01); *C07B 43/02* (2013.01); *C07B 43/06* (2013.01); *C07D 201/02* (2013.01); *B01J 29/06* (2013.01)

(58) Field of Classification Search
CPC .......... B01J 29/06; C07B 43/02; C07B 43/06; C07D 201/02; C07D 201/10
See application file for complete search history.

(56) References Cited

U.S. PATENT DOCUMENTS 3,505,191 A 4/1970 Williams et al.
3,544,438 A 12/1970 de Boer et al.
2011/0137027 A1 6/2011 Aubert
2016/0176797 A1 6/2016 Brueggemann et al.
2017/0081787 A1 3/2017 Son et al.
2017/0107168 A1 4/2017 Vautravers et al.
2017/0128916 A1 5/2017 Jejkowski et al.
2017/0129840 A1 5/2017 Hartmann et al.
2017/0129841 A1 5/2017 Hartmann et al.
2017/0175267 A1 6/2017 Strautmann et al.
2017/0183280 A1 6/2017 Vautravers et al.
2017/0197830 A1 7/2017 Riedel et al.
2017/0213654 A1 7/2017 Ootsuka
2017/0233865 A1 8/2017 Strautmann et al.
2017/0246620 A1 8/2017 Parvulescu et al.
2017/0275225 A1 9/2017 Riedel et al.
2017/0320847 A1 11/2017 Vautravers et al.
2017/0362532 A1 12/2017 Pelzer et al.
2018/0036723 A1 2/2018 Riedel et al.
2018/0134629 A1 5/2018 Kolios et al.
2018/0134646 A1 5/2018 Schaub et al.
2018/0170850 A1 6/2018 Vautravers et al.
2018/0186725 A1 7/2018 Schaub et al.
2018/0208745 A1 7/2018 Vautravers et al.
2018/0215694 A1 8/2018 Riedel et al.
2018/0215724 A1 8/2018 Gordillo et al.

(Continued)

FOREIGN PATENT DOCUMENTS

EP    0057143 A1   8/1982
EP    0076217 A2   4/1983

(Continued)

OTHER PUBLICATIONS

International Preliminary Report for Patentability with Written Opinion for International Application PCT/EP2017/051887, dated Aug. 16, 2018.
Mackor et al., "C-Nitroso Compounds Part. XI. Trans-azodioxycyclohexane (dimeric nitrosocyclohexane) by photochemical nitrosation of cyclohexane with alkyl nitrites", *Recueil*, vol. 88, pp. 1249-1262 (1969).
Ritz et al., "Caprolactam", *Ullmann's Encyclopedia of Industrial Chemistry*, vol. 00, 20 pages (2012).
International Search Report for PCT/EP2017/051887 dated Mar. 15, 2017.

(Continued)

*Primary Examiner* — Alexander R Pagano
*Assistant Examiner* — Ebenezer O Sackey
(74) *Attorney, Agent, or Firm* — Faegre Drinker LLP

(57) ABSTRACT

The present invention relates to a process for preparing $C_4$-$C_{15}$ lactams, in which a $C_1$-$C_{10}$-alkyl nitrite is reacted with a $C_4$-$C_{15}$-cycloalkane and is illuminated with a light-emitting diode during the reaction. This forms a $C_4$-$C_{15}$-cyclohexanone oxime which is then converted further to a $C_4$-$C_{15}$ lactam; the $C_1$-$C_{10}$ alcohol formed is recycled into the preparation of the $C_1$-$C_{10}$-alkyl nitrite.

12 Claims, No Drawings

(56) References Cited

U.S. PATENT DOCUMENTS

| | | |
|---|---|---|
| 2018/0230076 A1 | 8/2018 | Thrun et al. |
| 2018/0230117 A1 | 8/2018 | Teles et al. |
| 2018/0265443 A1 | 9/2018 | Vautravers et al. |
| 2018/0290959 A1 | 10/2018 | Thrun et al. |
| 2018/0297926 A1 | 10/2018 | Schaub et al. |

FOREIGN PATENT DOCUMENTS

| | | |
|---|---|---|
| EP | 0544530 A1 | 6/1993 |
| EP | 2868655 A1 | 5/2015 |
| WO | WO-2015197699 A1 | 12/2015 |
| WO | WO-201617776 A1 | 2/2016 |
| WO | WO-2016055452 A1 | 4/2016 |
| WO | WO-2016055453 A1 | 4/2016 |
| WO | WO-2016078960 A1 | 5/2016 |
| WO | WO-2017060437 A1 | 4/2017 |
| WO | WO-2017076942 A1 | 5/2017 |
| WO | WO-2017076947 A1 | 5/2017 |
| WO | WO-2017076956 A1 | 5/2017 |
| WO | WO-2017089327 A1 | 6/2017 |
| WO | WO-2017093265 A1 | 6/2017 |
| WO | WO-2017097806 A1 | 6/2017 |
| WO | WO-2017097835 A1 | 6/2017 |

OTHER PUBLICATIONS

Written Opinion of the International Searching Authority for PCT/EP2017/051887 dated Mar. 15, 2017.

METHOD FOR PRODUCING C4-C15 LACTAMS

CROSS-REFERENCE TO RELATED APPLICATIONS

This application is a national stage application (under 35 U.S.C. § 371) of PCT/EP2017/051892, filed Jan. 30, 2017, which claims benefit of European Application No. 16154181.8, filed Feb. 4, 2016, both of which are incorporated herein by reference in their entirety.

The present invention relates to a process for preparing $C_4$-$C_{15}$ lactams, in which a $C_1$-$C_{10}$-alkyl nitrite is reacted with a $C_4$-$C_{15}$-cycloalkane and is illuminated with a light-emitting diode during the reaction. This forms a $C_4$-$C_{15}$-cyclohexanone oxime which is then converted further to a $C_4$-$C_{15}$ lactam; the $C_1$-$C_{10}$ alcohol formed is recycled into the preparation of the $C_1$-$C_{10}$-alkyl nitrite.

Lactams, especially caprolactam, are of particular industrial significance for production of polyamides, especially nylon-6. The prior art describes various processes for preparing lactams, especially caprolactam.

For example, cyclohexane can be oxidized to cyclohexanone, followed by the preparation of a cyclohexanone oxime from the cyclohexanone, and finally caprolactam is prepared by a Beckmann rearrangement of the cyclohexanone oxime. This process is described, for example, in J. Ritz et al., "*Caprolactam*", *Ullmann's Encyclopedia of Industrial Chemistry*, 2012, Wiley-VCH.

U.S. Pat. No. 3,505,191 describes the preparation of cycloaliphatic ketoximes, proceeding from an alkyl nitrite and a cycloaliphatic hydrocarbon. The alkyl nitrite is reacted with the cycloaliphatic hydrocarbon to give the cycloaliphatic ketoxime. During the reaction, the mixture of the alkyl nitrite and the cycloaliphatic hydrocarbon is irradiated with γ radiation having a wavelength of less than 10 μm.

The use of γ rays is a matter of concern with regard to safety; moreover, the generation of γ radiation is very energy-intensive, which makes the process described in U.S. Pat. No. 3,505,191 extremely costly.

US 2011/0137027 describes the nitrosation of cycloalkanes proceeding from nitrosyl chloride, wherein the reaction is initiated with a light-emitting diode (LED). This forms an oxime hydrochloride which can then be converted by means of Beckmann rearrangement to a lactam.

US 2015/0175531 likewise describes the preparation of cycloalkanone oximes, proceeding from a cycloalkane and a nitrosating agent, wherein the reaction is initiated by an LED. Nitrosating agents described are nitrosyl chloride and trichloronitromethane. The cycloalkanone oxime that forms can then be converted by means of Beckmann rearrangement to a lactam.

A disadvantage of the processes described in US 2011/0137027 and US 2015/0175531 is that a relatively large number of chlorinated by-products are obtained, which have to be separated from the desired product in a complex manner. Moreover, the reaction forms hydrochloric acid, which attacks the materials of standard reactors, and so it is necessary to use reactors that are stable to hydrochloric acid and hence costly. Nitrosyl chloride is likewise corrosive and therefore likewise requires special reactor materials. This makes the processes described in US 2011/0137027 and US 2015/0175531 exceptionally costly.

A. Mackor et al., *Recueil* 1969, 88, 1249-1262, describe a process for photonitrosation of cyclohexane by means of tert-butyl nitrite, wherein the reaction is initiated by light from a mercury vapor lamp. The cyclohexanone oxime that forms can then be converted further to caprolactam. A disadvantage of the process described is that a very large number of by-products are formed, in particular many tars. This entails a complex purification of the products obtained, i.e. the cyclohexanone oxime and the caprolactam, and therefore makes the process very costly.

U.S. Pat. No. 3,544,438 likewise describes the photonitrosation of hydrocarbons, especially cycloalkanes, by means of nitrite esters, for example tert-butyl nitrite. The nitrosating is initiated by a light source with a wavelength in the region of below 400 nm. The process described in U.S. Pat. No. 3,544,438 also forms a large number of by-products, in particular many tars. This also entails a complex purification of the products obtained; moreover, some of the by-products are deposited on the lamp used, and so the light intensity thereof is reduced and the photonitrosation can be initiated only with difficulty thereby. It is necessary to change the lamp frequently. This too makes the process very costly.

It is therefore an object of the present invention to provide a process for preparing a lactam which has disadvantages of the processes as described in the prior art only to a reduced degree, if at all.

This object is achieved by a process for preparing $C_4$-$C_{15}$ lactams, comprising the steps of:

a) converting a first mixture (M1) comprising a $C_1$-$C_{10}$ alcohol, nitrogen oxides and oxygen to obtain a $C_1$-$C_{10}$-alkyl nitrite, b) converting a second mixture (M2) comprising the $C_1$-$C_{10}$-alkyl nitrite obtained in step a) and a $C_4$-$C_{15}$-cycloalkane to obtain a first product mixture (P1) comprising a $C_4$-$C_{15}$-nitrosocycloalkane, a dimeric $C_4$-$C_{15}$-nitrosocycloalkane, a $C_4$-$C_{15}$-cycloalkanone oxime and a $C_1$-$C_{10}$ alcohol, wherein the second mixture (M2) is illuminated during the conversion with a light-emitting diode that emits light having a wavelength in the range from 300 to 500 nm during the conversion, c) preparing the $C_4$-$C_{15}$ lactam by conversion of the $C_4$-$C_{15}$-cycloalkanone oxime obtained in step b) in the presence of a catalyst by one of the following steps:

c1) separating the $C_1$-$C_{10}$ alcohol from the first product mixture (P1) obtained in step b) to obtain a second product mixture (P2) comprising the $C_4$-$C_{15}$-cycloalkanone oxime, recycling the $C_1$-$C_{10}$ alcohol removed into the first mixture (M1) in step a) and converting the $C_4$-$C_{15}$-cycloalkanone oxime present in the second product mixture (P2) in the presence of the catalyst to obtain the $C_4$-$C_{15}$ lactam, or c2) converting the $C_1$-$C_{15}$-cycloalkanone oxime present in the first product mixture (P1) in the presence of the catalyst to obtain a third product mixture (P3) comprising the $C_4$-$C_{15}$ lactam and the $C_1$-$C_{10}$ alcohol, removing the $C_1$-$C_{10}$ alcohol present in the third product mixture (P3) to obtain the $C_1$-$C_{15}$ lactam and recycling the $C_1$-$C_{10}$ alcohol removed into the first mixture (M1) in step a).

It has been found that, surprisingly, the process of the invention forms a much lower level of by-products in the preparation of the $C_4$-$C_{15}$ lactam and can therefore achieve higher selectivities for the $C_4$-$C_{15}$ lactam than in the processes as described in the prior art. Moreover, the $C_4$-$C_{15}$ lactam prepared in accordance with the invention and the $C_4$-$C_{15}$-nitrosocycloalkane prepared as intermediate has a high purity and therefore requires only a small degree of purification, if any. Moreover, the $C_1$-$C_{10}$ alcohol obtained in the nitrosation in step b) can be recycled into step a) and be reused therein for preparation of $C_1$-$C_{10}$-alkyl nitrites. This makes the process of the invention particularly efficient.

In addition, the process of the invention does not use any aggressive chemicals, such as nitrosyl chloride, and none of the reactants comprises chlorine. Therefore, no chlorinated by-products that can be removed from the product mixtures only with difficulty are obtained either.

Since no aggressive chemicals are used, no particular demands are made on the reactors either, which makes the process of the invention extremely inexpensive in apparatus terms.

A further advantage is that light-emitting diodes, which are particularly energy-efficient and economical, are used in the process of the invention. This distinctly reduces the energy consumption of the process of the invention, especially compared to the processes described in the prior art in which mercury vapor lamps are used.

A further advantage is that the light-emitting diodes do not require any cooling and, because of their simple design, are therefore usable in a flexible manner and enable a simple reactor design.

The process of the invention is elucidated in detail hereinafter.

Step a)

In step a), a first mixture (M1) is converted to obtain a $C_1$-$C_{10}$-alkyl nitrite. The first mixture (M1) comprises a $C_1$-$C_{10}$ alcohol, nitrogen oxides and oxygen.

"A $C_1$-$C_{10}$ alcohol" in the context of the present invention means either exactly one $C_1$-$C_{10}$ alcohol or a mixture of two or more $C_1$-$C_{10}$ alcohols. Preference is given to exactly one $C_1$-$C_{10}$ alcohol.

According to the invention, the first mixture (M1) comprises a $C_1$-$C_{10}$ alcohol, preferably a $C_1$-$C_8$ alcohol and especially preferably a $C_1$-$C_5$ alcohol.

$C_1$-$C_{10}$ alcohol in the context of the present invention is understood to mean monoalcohols comprising 1 to 10 carbon atoms. Monoalcohols are alcohols having exactly one hydroxyl group.

The $C_1$-$C_{10}$ alcohols may additionally have further substituents that do not take part in the reaction in step a), step b) or step c). Preferably, $C_1$-$C_{10}$ alcohols are unsubstituted.

Corresponding details apply to $C_1$-$C_8$ alcohol and $C_1$-$C_5$ alcohol.

Preferred $C_1$-$C_{10}$ alcohols are selected from the group consisting of methanol, ethanol, propanols, butanols, pentanols, hexanols, heptanols, octanols, nonanols and decanols.

Preferred $C_1$-$C_8$ alcohols are selected from the group consisting of methanol, ethanol, propanols, butanols, pentanols, hexanols, heptanols and octanols.

Preferred $C_1$-$C_5$ alcohols are selected from the group consisting of methanol, ethanol, propanols, butanols and pentanols.

The terms "propanols", "butanols", "pentanols", "hexanols", "heptanols", "octanols", "nonanols" and "decanols" in the context of the present invention encompass all isomers of the corresponding monoalcohols.

The term "propanols" therefore encompasses, for example, both n-propanol and isopropanol.

The term "butanols" in the context of the present invention therefore encompasses, for example, n-butanol, isobutanol, sec-butanol and tert-butanol.

The term "pentanols" in the context of the present invention encompasses, for example, n-pentanol, 2-pentanol, 3-pentanol, 2-methyl-1-butanol, tert-pentanol, isopentanol, 3-methyl-2-butanol and neopentanol.

Analogous details apply to hexanols, heptanols, octanols, nonanols and decanols.

More preferably, the $C_1$-$C_{10}$ alcohol is selected from the group consisting of methanol, ethanol, n-propanol, isopropanol, n-butanol, sec-butanol, tert-butanol, n-pentanol, 2-pentanol, 3-pentanol, 2-methyl-1-butanol, tert-pentanol, isopentanol, 3-methyl-2-butanol and neopentanol.

Most preferably, the $C_1$-$C_{10}$ alcohol in step a) is selected from the group consisting of methanol, tert-butanol and neopentanol.

The present invention therefore also provides a process in which the $C_1$-$C_{10}$ alcohol present in the first mixture (M1) in step a) is selected from the group consisting of methanol, tert-butanol and neopentanol.

According to the invention, the first mixture (M1), apart from the $C_1$-$C_{10}$ alcohol, comprises nitrogen oxides and oxygen.

Nitrogen oxides of the invention are at least one compound selected from the group consisting of nitrogen monoxide (NO), nitrogen dioxide ($NO_2$), dinitrogen trioxide ($N_2O_3$) and dinitrogen pentoxide ($N_2O_5$).

Nitrogen dioxide, dinitrogen trioxide and dinitrogen pentoxide are typically obtained by contacting nitrogen monoxide with oxygen. In this case, the nitrogen monoxide reacts at least partly with oxygen to obtain nitrogen dioxide, dinitrogen trioxide and/or dinitrogen pentoxide.

The molar ratio of nitrogen oxides to oxygen in the first mixture (M1) is, for example, in the range from 1 to 10, preferably in the range from 2 to 10 and especially preferably in the range from 4 to 10. It is additionally preferable that the molar ratio of nitrogen oxides to oxygen in the first mixture (M1) is ≥4.

The molar ratio of the $C_1$-$C_{10}$ alcohol to the oxygen in the first mixture (M1) is, for example, in the range from 1 to 10, preferably in the range from 2 to 8 and especially preferably in the range from 3 to 7.

In addition, the first mixture (M1) may comprise, for example, inert gases. Inert gases which may be present in the first mixture (M1) are understood to mean gases which behave in an inert manner under the conditions under which the first mixture (M1) is converted. Inert gases of this kind are known to those skilled in the art. Suitable inert gases are, for example, nitrogen or carbon dioxide.

For example, the first mixture (M1) comprises in the range from 1% to 99% by volume of inert gases, preferably in the range from 10% to 95% by volume and especially preferably in the range from 30% to 90% by volume, based in each case on the total volume of the first mixture (M1).

The conversion of the first mixture (M1) is known as such to the person skilled in the art and is described, for example, in EP 0 057 143 and in EP 0 076 217.

The conversion of the first mixture (M1) can be effected at any temperature at which the $C_1$-$C_{10}$ alcohol present in the first mixture (M1) reacts with the nitrogen oxides and the oxygen. For example, the conversion of the first mixture (M1) in step a) is conducted at a temperature in the range from 10 to 300° C., preferably in the range from 20 to 130° C. and especially preferably in the range from 50 to 110° C.

The present invention therefore also provides a process in which the conversion of the first mixture (M1) in step a) is conducted at a temperature in the range from 10 to 300° C.

The pressure during the conversion of the first mixture (M1) in step a) is, for example, in the range from 1 to 50 bar, preferably in the range from 1 to 10 bar and especially preferably in the range from 1 to 5 bar.

The present invention therefore also provides a process in which the conversion of the first mixture (M1) in step a) is conducted at a pressure in the range from 1 to 50 bar.

The conversion of the first mixture (M1) in step a) is typically effected in a first reactor. Suitable first reactors are all reactors that are known to those skilled in the art and are suitable for use at the temperatures and pressures used in step a). Reactors of this kind are known to those skilled in the art and are, for example, flow tube reactors.

The first mixture (M1) can be supplied to the first reactor by all methods known to those skilled in the art. Preferably, the $C_1$-$C_{10}$ alcohol is supplied to the first reactor separately from the nitrogen oxides and the oxygen.

It is additionally preferable that the $C_1$-$C_{10}$ alcohol is supplied to the first reactor separately from the nitrogen oxides and the oxygen, in which case, in a first step, nitrogen monoxide is supplied to the reactor with oxygen and they react at least partially to obtain the nitrogen oxides and the oxygen and only then are contacted with the $C_1$-$C_{10}$ alcohol.

The nitrogen oxides and the oxygen are supplied to the first reactor typically in gaseous form, and the $C_1$-$C_{10}$ alcohol typically in liquid form.

In step a), a $C_1$-$C_{10}$-alkyl nitrite is obtained. It will be clear to the person skilled in the art that a $C_1$-$C_{10}$-alkyl nitrite that derives from the $C_1$-$C_{10}$ alcohol present in the first mixture (M1) is obtained. Thus, for example, if the $C_1$-$C_{10}$ alcohol used is methanol, the $C_1$-$C_{10}$-alkyl nitrite obtained is methyl nitrite. If, for example, tert-butanol is used as $C_1$-$C_{10}$ alcohol, the $C_1$-$C_{10}$-alkyl nitrite obtained is tert-butyl nitrite, and when the $C_1$-$C_{10}$ alcohol used is neopentanol, the $C_1$-$C_{10}$-alkyl nitrite obtained is 2,2-dimethyl-1-propyl nitrite.

In the reaction of the $C_1$-$C_{10}$ alcohol with nitrogen oxides and oxygen, apart from the $C_1$-$C_{10}$-alkyl nitrite, water is additionally obtained. This reaction is known as such to the person skilled in the art and is described, for example, in EP 0 057 143 and EP 0 076 217.

The $C_1$-$C_{10}$-alkyl nitrite obtained is preferably separated from the water formed and any unreacted $C_1$-$C_{10}$ alcohol prior to the further conversion in step b).

Processes for this purpose are known to those skilled in the art. For example, the separation can be effected by distillation. This affords the $C_1$-$C_{10}$-alkyl nitrite as the top product; water and unreacted $C_1$-$C_{10}$ alcohol remain in the bottom product. The unreacted $C_1$-$C_{10}$ alcohol can be recycled into the first mixture (M1) in step a), optionally after prior purification.

Step b)

In step b), a second mixture (M2) is converted to obtain a first product mixture (P1), wherein the second mixture (M2) is illuminated during the conversion with a light-emitting diode that emits light having a wavelength in the range from 300 to 500 nm, preferably in the range from 340 to 390 nm and more preferably in the range from 350 to 370 nm.

The second mixture (M2) comprises the $C_1$-$C_{10}$-alkyl nitrite obtained in step a) and a $C_4$-$C_{15}$-cycloalkane.

"A $C_4$-$C_{15}$-cycloalkane" in the context of the present invention means either exactly one $C_4$-$C_{15}$-cycloalkane or a mixture of two or more $C_4$-$C_{15}$-cycloalkanes.

The second mixture (M2) comprises a $C_4$-$C_{15}$-cycloalkane, preferably a $C_5$-$C_{12}$-cycloalkane and especially preferably a $C_6$-$C_{12}$-cycloalkane.

"$C_4$-$C_{15}$-cycloalkane" in the context of the present invention is understood to mean cyclic saturated hydrocarbons having 4 to 15 carbon atoms. The hydrocarbons may additionally be substituted. They are preferably unsubstituted. Corresponding details apply to $C_5$-$C_{12}$-cycloalkane and $C_6$-$C_{12}$-cycloalkane.

The $C_4$-$C_{15}$-cycloalkane is preferably selected from the group consisting of cyclobutane, cyclopentane, cyclohexane, cycloheptane, cyclooctane and cyclododecane.

More preferably, the $C_4$-$C_{15}$-cycloalkane is selected from the group consisting of cyclopentane, cyclohexane and cyclododecane; the $C_4$-$C_{15}$-cycloalkane in step b) is especially preferably selected from the group consisting of cyclohexane and cyclododecane.

The present invention thus also provides a process in which the $C_4$-$C_{15}$-cycloalkane in step b) is selected from the group consisting of cyclopentane, cyclohexane and cyclododecane.

The second mixture (M2) may comprise the $C_1$-$C_{10}$-alkyl nitrite present in step a) and the $C_4$-$C_{15}$-cycloalkane in any desired molar ratios.

For example, the molar ratio of $C_1$-$C_{10}$-alkyl nitrite $C_4$-$C_{15}$-cycloalkane in the second mixture (M2) is in the range from 1:1 to 1:100, preferably in the range from 1:2 to 1:50 and most preferably in the range from 1:5 to 1:30.

The present invention therefore also provides a process in which the second mixture (M2) comprises the $C_1$-$C_{10}$-alkyl nitrite obtained in step a) and the $C_4$-$C_{15}$-cycloalkane in a molar ratio of $C_1$-$C_{10}$-alkyl nitrite to $C_4$-$C_{15}$-cycloalkane in the range from 1:1 to 1:100.

The conversion of the second mixture (M2) in step b) is typically effected at a temperature in the range from −30 to 150° C., preferably in the range from 0 to 120° C. and especially preferably in the range from 0 to 80° C.

The present invention thus also provides a process in which the conversion of the second mixture (M2) in step b) is conducted at a temperature in the range from −30 to 150° C.

The pressure in the conversion of the second mixture (M2) in step b) is typically in the range from 1 to 10 bar, preferably in the range from 1 to 6 bar and especially preferably in the range from 1 to 3 bar.

The present invention thus also provides a process in which the conversion of the second mixture (M2) in step b) is conducted at a pressure in the range from 1 to 10 bar.

During the conversion of the second mixture (M2), the second mixture (M2) is illuminated with a light-emitting diode that emits light having a wavelength in the range from 300 to 500 nm, preferably having a wavelength in the range from 340 to 390 nm and especially preferably in the range from 350 to 370 nm.

The present invention therefore also provides a process in which the light-emitting diode in step b) emits light having a wavelength in the range from 340 to 390 nm.

Light-emitting diodes (LEDs) are known as such to those skilled in the art.

A light-emitting diode typically has an emission spectrum having an emission band with an emission maximum. If the light-emitting diode emits light having a wavelength in the range from 300 to 500 nm, preferably in the range from 340 to 390 nm and especially preferably in the range from 350 to 370 nm, this means in the context of the present invention that the maximum of the emission band is in the range from 300 to 500 nm, preferably in the range from 340 to 390 nm and especially preferably in the range from 350 to 370 nm.

It is also preferable that the light-emitting diode has an emission maximum in the region of the absorption band of the n-π* transition of the $C_1$-$C_{10}$-alkyl nitrite.

The n-π* transition of the $C_1$-$C_{10}$-alkyl nitrite is known to those skilled in the art. The n-π* transition is understood to mean the electronic transition of an electron from a non-bonding orbital of the nitrite group of the $C_1$-$C_{10}$-alkyl nitrite to an anti-bonding $\pi^*$ orbital. The absorption region of the n-$\pi^*$ transition is typically in the range from 300 to 500 nm, preferably in the range from 340 to 390 nm and especially preferably in the range from 350 to 370 nm.

It is thought that, when the second mixture (M2) is illuminated with the light-emitting diode during the conversion, the $C_1$-$C_{10}$-alkyl nitrite present in the second mixture (M2) is photochemically cleaved to obtain a nitrosyl radical and a $C_1$-$C_{10}$-alkoxy radical.

The $C_1$-$C_{10}$-alkoxy radical abstracts a hydrogen radical from the $C_4$-$C_{15}$-cycloalkane to obtain a $C_1$-$C_{10}$ alcohol and a $C_4$-$C_{15}$-cycloalkyl radical, while the nitrosyl radical adds onto the $C_4$-$C_{15}$-cycloalkyl radical as it forms to obtain the $C_4$-$C_{15}$-nitrosocycloalkane.

The $C_4$-$C_{15}$-nitrosocycloalkane obtained isomerizes and then typically at least partly dimerizes under the conditions in step b). This forms a dimeric $C_4$-$C_{15}$-nitrosocycloalkane and a $C_4$-$C_{15}$-cycloalkanone oxime. The dimeric $C_4$-$C_{15}$-nitrosocycloalkane has the following structural formula:

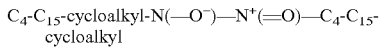

This means that, for example, a dimeric nitrosocyclohexane has the following structural formula:

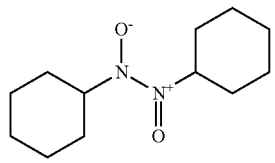 [SMILES: O=[N+](C1CCCCC1)N([O-])C1CCCCC1]

The first product mixture (P1) therefore comprises the $C_4$-$C_{15}$-nitrosocycloalkane, the dimeric $C_4$-$C_{15}$-nitrosocycloalkane, the $C_4$-$C_{15}$-cycloalkanone oxime and the $C_1$-$C_{10}$ alcohol.

The $C_1$-$C_{10}$ alcohol is derived from the $C_1$-$C_{10}$-alkyl nitrite and therefore corresponds to the $C_1$-$C_{10}$ alcohol used in step a). In respect of the $C_1$-$C_{10}$ alcohol obtained in step b), therefore, the above-described details and preferences for the $C_1$-$C_{10}$ alcohol present in the first mixture (M1) in step a) apply correspondingly.

The $C_4$-$C_{15}$-nitrosocycloalkane present in the first product mixture (P1) is derived from the $C_4$-$C_{15}$-cycloalkane.

It will therefore be apparent that, when a preferred $C_5$-$C_{12}$-cycloalkane is present in the second mixture (M2), a $C_5$-$C_{12}$-nitrosocycloalkane is obtained in the first product mixture (P1). If a particularly preferred $C_6$-$C_{12}$-cycloalkane is present in the second mixture (M2), the first product mixture (P1) comprises a $C_6$-$C_{12}$-nitrosocycloalkane.

If the $C_4$-$C_{15}$-cycloalkane used, therefore, is cyclopentane for example, the $C_4$-$C_{15}$-nitrosocycloalkane formed is nitrosocyclopentane. If the $C_4$-$C_{15}$-cycloalkane is cyclohexane, the $C_4$-$C_{15}$-nitrosocycloalkane formed is nitrosocyclohexane. If cyclododecane is used as the $C_4$-$C_{15}$-cycloalkane, nitrosocyclododecane is the $C_4$-$C_{15}$-nitrosocycloalkane that forms.

A $C_4$-$C_{15}$-nitrosocycloalkane is understood in the context of the present invention to mean a $C_4$-$C_{15}$-cycloalkane in which one of the hydrogen atoms has been replaced (substituted) by a nitroso group (—N=O).

The $C_4$-$C_{15}$-nitrosocycloalkane obtained can then dimerize to give a dimeric $C_4$-$C_{15}$-nitrosocycloalkane. It will be apparent that, when a $C_5$-$C_{12}$-nitrosocycloalkane dimerizes, a dimeric $C_5$-$C_{12}$-nitrosocycloalkane forms and, correspondingly, when a $C_6$-$C_{12}$-nitrosocycloalkane dimerizes, a dimeric $C_5$-$C_{12}$-nitrosocycloalkane is obtained.

Corresponding details apply to the $C_4$-$C_{15}$-cycloalkanone oxime obtained by isomerization of the $C_4$-$C_{15}$-nitrosocycloalkane. When a $C_5$-$C_{12}$-nitrosocycloalkane is obtained, it isomerizes to give a $C_5$-$C_{12}$-cycloalkanone oxime. If a $C_6$-$C_{12}$-nitrosocycloalkane is obtained, it isomerizes to give $C_6$-$C_{12}$-cycloalkanone oxime.

Thus, if nitrosocyclopentane is obtained as the $C_4$-$C_{15}$-nitrosocycloalkane, it isomerizes to give cyclopentanone oxime. If nitrosocyclohexane is obtained as the $C_4$-$C_{15}$-nitrosocycloalkane, it isomerizes to give cyclohexanone oxime, and, if nitrosocyclododecane is obtained as the $C_4$-$C_{15}$-nitrosocycloalkane, it isomerizes to give cyclododecanone oxime.

The first product mixture (P1) may additionally comprise unconverted $C_4$-$C_{15}$-cycloalkane. The unconverted $C_4$-$C_{15}$-cycloalkane which may be present in the first product mixture (P1) is preferably removed prior to step c) from the first product mixture (P1) and recycled into step b). Processes for removing the $C_4$-$C_{15}$-cycloalkane are known as such to the person skilled in the art.

The conversion of the second mixture (M2) in step b) can take place in all reactors known to those skilled in the art. Preference is given to using a second reactor other than the first reactor in step a).

The second mixture (M2) can be stirred during the conversion in step b).

The present invention therefore also provides a process in which the second mixture (M2) is stirred during the reaction in step b).

Processes for stirring the second mixture (M2) in step b) are known to those skilled in the art. Suitable stirrers are likewise known to those skilled in the art and are, for example, magnetic stirrers.

It is additionally possible that the conversion of the second mixture (M2) in step b) takes place in the presence of a solvent. Suitable solvents are, for example, selected from the group consisting of benzene and alcohols.

The components present in the second mixture (M2), the $C_1$-$C_{10}$-alkyl nitrite and the $C_4$-$C_{15}$-cycloalkane, can be supplied to the second reactor by any methods known to those skilled in the art. For example, the $C_1$-$C_{10}$-alkyl nitrite and the $C_4$-$C_{15}$-cycloalkane can be supplied separately to the second reactor. It is likewise possible and preferable in accordance with the invention that the $C_1$-$C_{10}$-alkyl nitrite and the $C_4$-$C_{15}$-cycloalkane are mixed with one another outside the second reactor to obtain the second mixture (M2) and then the second mixture (M2) is supplied to the second reactor.

Step c)

In step c), $C_4$-$C_{15}$ lactam is prepared by converting the $C_4$-$C_{15}$-cycloalkanone oxime obtained in step b) in the presence of a catalyst.

This reaction is known as such to the person skilled in the art and is described, for example, in EP 0 544 530 and in J. Ritz et al., "*Caprolactam*", *Ullmann's Encyclopedia of Industrial Chemistry,* 2012, Wiley-VCH.

"A catalyst" in the context of the present invention means either exactly one catalyst or two or more catalysts.

Suitable catalysts in step c) are all catalysts which are known to those skilled in the art and catalyze the conversion of the $C_4$-$C_{15}$-cycloalkanone oxime to the $C_4$-$C_{15}$ lactam.

Catalysts of this kind are selected, for example, from the group consisting of zeolites and inorganic acids.

The present invention therefore also provides a process in which the catalyst in step c) is selected from the group consisting of zeolites and inorganic acids.

Suitable zeolites as catalyst in step c) are known to those skilled in the art and are, for example, metal silicates as described in EP 0 544 530.

Suitable inorganic acids as catalyst in step c) are likewise known to those skilled in the art and are, for example, sulfuric acid and/or phosphoric acid.

The temperature during the conversion of the $C_4$-$C_{15}$-cycloalkanone oxime in step c) is, for example, in the range from 50 to 500° C., preferably in the range from 70 to 450° C. and especially preferably in the range from 90 to 400° C.

The present invention therefore also provides a process in which the conversion of the $C_4$-$C_{15}$-cycloalkanone oxime in step c) is conducted at a temperature in the range from 50 to 500° C.

The temperature during the conversion of the $C_4$-$C_{15}$-cycloalkanone oxime in step c), when it is effected in the presence of a zeolite as catalyst, is typically in the range from 250 to 500° C., preferably in the range from 275 to 450° C. and especially preferably in the range from 300 to 400° C.

If the conversion of the $C_4$-$C_{15}$-cycloalkanone oxime in step c) is effected in the presence of an inorganic acid as catalyst, the temperature during the conversion is typically in the range from 50 to 200° C., preferably in the range from 70 to 160° C. and especially preferably in the range from 90 to 120° C.

If the conversion of the $C_4$-$C_{15}$-cycloalkanone oxime is effected in the presence of zeolites as catalyst, it is also preferable that the conversion is effected with addition of water. For example, 0.06 to 2.5 mol, preferably 0.18 to 1.9 mol and especially preferably 0.18 to 0.65 mol of water are used per mole of $C_4$-$C_{15}$-cycloalkanone oxime which is converted.

The pressure during the conversion of the $C_4$-$C_{15}$-cycloalkanone oxime in step c) is, for example, in the range from 0.05 to 10 bar, preferably in the range from 0.5 to 7 bar and especially preferably in the range from 1 to 5 bar.

The present invention therefore also provides a process in which the conversion of the $C_4$-$C_{15}$-cycloalkanone oxime in step c) is conducted at a pressure in the range from 0.05 to 10 bar.

The $C_4$-$C_{15}$-cycloalkanone oxime may be in gaseous or liquid form during the conversion in step c). Preferably, the $C_4$-$C_{15}$-cycloalkanone oxime is in liquid form during the conversion in step c) when the catalyst is selected from the group consisting of inorganic acids.

The $C_4$-$C_{15}$-cycloalkanone oxime is in gaseous form, for example, during the conversion when the catalyst in step c) is selected from the group consisting of zeolites. This embodiment is preferred.

The present invention therefore also provides a process in which the $C_4$-$C_{15}$-cycloalkanone oxime is in gaseous form during the conversion of the $C_4$-$C_{15}$-cycloalkanone oxime in step c).

The present invention further provides a process in which the catalyst in step c) is selected from the group consisting of zeolites, and in which the $C_4$-$C_{15}$-cycloalkanone oxime is in gaseous form during the conversion of the $C_4$-$C_{15}$-cycloalkanone oxime in step c).

The conversion of the $C_4$-$C_{15}$-cycloalkanone oxime affords a $C_4$-$C_{15}$ lactam.

$C_4$-$C_{15}$ lactams of this kind are known to those skilled in the art. $C_4$-$C_{15}$ lactams are cyclic amides having 4 to 15 carbon atoms in the ring. The $C_4$-$C_{15}$ lactams obtained are, for example, selected from the group consisting of 4-aminobutanolactam (γ-lactam; γ-butyrolactam; pyrrolidone), 5-aminopentanolactam (δ-lactam; δ-valerolactam; piperidone), 6-aminohexanolactam (ε-lactam; ε-caprolactam), 7-aminoheptanolactam (ζ-lactam; ζ-heptanolactam; enantholactam), 8-aminooctanolactam (η-lactam; η-octanolactam; caprylolactam), 9-nonanolactam (θ-lactam; θ-nonanolactam), 10-decanolactam (ω-decanolactam; caprinolactam), 11-undecanolactam (ω-undecanolactam) and 12-dodecanolactam (ω-dodecanolactam; laurolactam).

The $C_4$-$C_{15}$ lactam obtained in the conversion of the $C_4$-$C_{15}$-cycloalkanone oxime derives from the $C_4$-$C_{15}$-cycloalkanone oxime.

It will therefore be apparent that, when a $C_5$-$C_{12}$-cycloalkanone oxime is used, a $C_5$-$C_{12}$ lactam is obtained. If a $C_6$-$C_{12}$-cycloalkanone oxime is used, a $C_6$-$C_{12}$ lactam is obtained.

If the $C_4$-$C_{15}$-cycloalkanone oxime used is, for example, cyclopentanone oxime, piperidone is obtained as the $C_4$-$C_{15}$ lactam. If the $C_4$-$C_{15}$-cycloalkanone oxime is cyclohexanone oxime, caprolactam is obtained as the $C_4$-$C_{15}$ lactam. If cyclododecanone oxime is used as the $C_4$-$C_{15}$-cycloalkanone oxime, laurolactam is obtained as the $C_4$-$C_{15}$ lactam.

During the conversion of the $C_4$-$C_{15}$-cycloalkanone oxime typically also at least the $C_4$-$C_{15}$-nitrosocycloalkane present in the first product mixture (P1) and the dimeric $C_4$-$C_{15}$-nitrosocycloalkane present in the first product mixture (P1) are present. The $C_4$-$C_{15}$-nitrosocycloalkane and the dimeric $C_4$-$C_{15}$-nitrosocycloalkane typically likewise isomerize during the conversion of the $C_4$-$C_{15}$-cycloalkanone oxime to give the $C_4$-$C_{15}$-cycloalkanone oxime and can then likewise react to give the $C_4$-$C_{15}$ lactam.

The preparation of the $C_4$-$C_{15}$ lactam in step c) is effected either by step c1) or by step c2).

Step c1)

In step c1), the $C_1$-$C_{10}$ alcohol is first separated from the first product mixture (P1) obtained in step b), giving a second product mixture (P2) comprising the $C_4$-$C_{15}$-cycloalkanone oxime. The $C_1$-$C_{10}$ alcohol separated is then recycled into the first mixture (M1) in step a) and the $C_4$-$C_{15}$-cycloalkanone oxime present in the second product mixture (P2) is converted in the presence of the catalyst to obtain the $C_4$-$C_{15}$ lactam.

The $C_1$-$C_{10}$ alcohol can be separated from the first product mixture (P1) obtained in step b) by any methods known to those skilled in the art, for example by distillation.

This affords the second product mixture (P2) comprising the $C_4$-$C_{15}$-cycloalkanone oxime. The second product mixture (P2) may additionally comprise residues of the $C_1$-$C_{10}$ alcohol.

The $C_4$-$C_{15}$-nitrosocycloalkane likewise present in the first product mixture (P1), and also the dimeric $C_4$-$C_{15}$-nitrosocycloalkane likewise present in the first product mixture (P1), are typically not removed with the $C_1$-$C_{10}$ alcohol and therefore remain in the second product mixture (P2).

The present invention therefore also provides a process in which the second product mixture (P2) comprises the $C_4$-$C_{15}$-cycloalkanone oxime, the $C_4$-$C_{15}$-nitrosocycloalkane and the dimeric $C_4$-$C_{15}$-nitrosocycloalkane.

The $C_1$-$C_{10}$ alcohol removed is recycled into the first mixture (M1) in step a). Processes for recycling the $C_1$-$C_{10}$ alcohol removed are known as such to those skilled in the art. Optionally, the $C_1$-$C_{10}$ alcohol removed can be purified prior to recycling into the first mixture (M1) in step a). Processes for purifying the $C_1$-$C_{10}$ alcohol are known as such to those skilled in the art. The purification can be effected, for example, by means of distillation.

In respect of the conversion of the $C_4$-$C_{15}$-cycloalkanone oxime present in the second product mixture (P2) in the presence of the catalyst to obtain the $C_4$-$C_{15}$ lactam, the details and preferences described above apply.

The above-described details and preferences likewise apply to the catalyst.

Step c2)

In step c2), the $C_4$-$C_{15}$-cycloalkanone oxime present in the first product mixture (P1) is first converted in the presence of the catalyst to obtain a third product mixture (P3) comprising the $C_4$-$C_{15}$ lactam and the $C_1$-$C_{10}$ alcohol. Subsequently, the $C_1$-$C_{10}$ alcohol is separated from the third product mixture (P3) to obtain the $C_4$-$C_{15}$ lactam, and then the $C_1$-$C_{10}$ alcohol removed is recycled into the first mixture (M1) in step a).

In respect of the conversion of the $C_4$-$C_{15}$-cycloalkanone oxime present in the first product mixture (P1), and likewise for the catalyst, the above-described details and preferences apply.

The $C_1$-$C_{10}$ alcohol can be separated from the third product mixture (P3) obtained by any methods known to those skilled in the art, for example by distillation.

This affords the $C_4$-$C_{15}$ lactam. The $C_4$-$C_{15}$ may additionally comprise residues of the $C_1$-$C_{10}$ alcohol.

Preferably, the $C_4$-$C_{15}$ lactam does not comprise any residues of the $C_1$-$C_{10}$ alcohol.

The $C_1$-$C_{10}$ alcohol removed is recycled into the first mixture (M1) in step a). Processes for recycling the $C_1$-$C_{10}$ alcohol removed are known as such to those skilled in the art. Optionally, the $C_1$-$C_{10}$ alcohol removed can be purified prior to recycling into the first mixture (M1) in step a). Processes for purifying the $C_1$-$C_{10}$ alcohol are known as such to those skilled in the art. For example, the purification can be effected by means of distillation.

The present invention is elucidated in detail hereinafter by examples without restricting it thereto.

EXAMPLES

Examples I1 to I6 tert-Butyl nitrite (90% by weight in tert-butanol, Sigma-Aldrich) and cyclohexane (Sigma-Aldrich), in the ratio specified in table 1, were illuminated in a borosilicate tube sealed with a Teflon screwtop at room temperature (20° C.) while stirring for 16 hours. Illumination was effected using a light-emitting diode (Nichia SMD LED UV NVSU233a) which emits light having a wavelength of 365 nm and has light intensity 1 W at 3.7 V and 1 A, applied to an aluminum heatsink. This formed the first product mixture. For determination of nitrosocyclohexane and cyclohexanone oxime in the first product mixture formed, 0.08 ml of the first product mixture was dissolved in 0.8 ml of benzene-$d_6$, and 0.01 ml of mesitylene was added as internal standard. Subsequently, the content of nitrosocyclohexane and the cyclohexanone oxime was determined by means of $^1$H NMR spectroscopy.

TABLE 1

| Example | tert-Butyl nitrite [mol] | Cyclohexane [mol] | Nitrosocyclohexane [%] | Cyclohexanone oxime [%][1] |
| --- | --- | --- | --- | --- |
| I1 | 0.2 | 10 | n.d. | 49.8 |
| I2 | 0.25 | 10 | n.d. | 40.0 |

TABLE 1-continued

| Example | tert-Butyl nitrite [mol] | Cyclohexane [mol] | Nitrosocyclohexane [%] | Cyclohexanone oxime [%][1] |
| --- | --- | --- | --- | --- |
| I3 | 0.33 | 10 | n.d. | 45.5 |
| I4 | 0.5 | 10 | n.d. | 40.2 |
| I5 | 0.67 | 10 | 15.8 | 32.3 |
| I6 | 1.2 | 8.4 | 19.2 | 32.3 |

[1]The percentages are based on the crude yield of nitrosocyclohexane or of cyclohexanone oxime based on tert-butyl nitrite Example 17 tert-Butyl nitrite (90% by weight in tert-butanol; 2.5 mmol, 0.33 ml; Sigma-Aldrich) and cyclohexane (50 mmol, 5.41 ml; Sigma-Aldrich) was illuminated in a closed borosilicate glass tube while stirring for 16 hours to obtain the first product mixture. The light source used was a light-emitting diode which emits light having a wavelength of 365 nm (Nichia SMD LED UV NVSU233a having a light intensity of 1 W at 3.7 V and 1 A).

For determination of nitrosocyclohexane and cyclohexanone oxime in the first product mixture formed, 0.08 ml of the first product mixture was dissolved in 0.8 ml of benzene-$d_6$, and 0.01 ml of mesitylene was added as internal standard. Subsequently, the content of nitrosocyclohexane and the cyclohexanone oxime was determined by means of $^1$H NMR spectroscopy. Crude yields of 19% nitrosocyclohexane and 38% cyclohexanone oxime based on tert-butyl nitrite were obtained in the first product mixture.

After the reaction, all volatile constituents were removed from the first product mixture (P1) obtained and a mixture of nitrosocyclohexane and cyclohexanone oxime was obtained as a solid residue. This mixture was purified by means of column chromatography on silica gel with a 4:1 mixture of petroleum ether and ethyl acetate and then the composition of the product was determined by $^1$H NMR spectroscopy, mass spectroscopy and elemental analysis. In relation to the nitrite used, 48% cyclohexanone oxime and 8% nitrosocyclohexane were obtained.

Examples I8 to I27

A second mixture consisting of tert-butyl nitrite (90% by weight in tert-butanol, Sigma-Aldrich; 0.5 mmol) and cyclohexane (Sigma-Aldrich; 10 mmol) was illuminated in a borosilicate tube sealed with a Teflon screwtop at 25° C. (table 2) and at 50° C. (table 3) while stirring for the periods of time specified in tables 2 and 3 (reaction time). Illumination was effected using a light-emitting diode (Nichia SMD LED UV NVSU233a) which emits light having a wavelength of 365 nm and has light intensity 1 W at 3.7 V and 1 A, applied to an aluminum heatsink. This formed the first product mixture. The determination of nitrosocyclohexane and cyclohexanone oxime in the first product mixture formed was effected as described in examples B1 to B6 by means of $^1$H NMR spectroscopy.

The crude yields achieved as a function of reaction time are shown in tables 2 and 3.

TABLE 2

| Example | Reaction time [h] | Nitrosocyclohexane [%] | Cyclohexanone oxime [%][1] |
|---|---|---|---|
| I8 | 0.25 | 23 | — |
| I9 | 0.5 | 29 | — |
| I10 | 1 | 37 | 5 |
| I11 | 1.5 | 45 | 9 |
| I12 | 2 | 45 | 9 |
| I13 | 3 | 33 | 7 |
| I14 | 4 | 29 | 14 |
| I15 | 5 | 27 | 25 |
| I16 | 6 | 14 | 36 |

[1]The percentages are based on the crude yield of nitrosocyclohexane or of cyclohexanone oxime based on tert-butyl nitrite

TABLE 3

| Example | Reaction time [min] | Nitrosocyclohexane [%] | Cyclohexanone oxime [%][1] |
|---|---|---|---|
| I17 | 5 | — | — |
| I18 | 10 | — | — |
| I19 | 15 | 6 | — |
| I20 | 20 | 16 | — |
| I21 | 30 | 23 | — |
| I22 | 45 | 25 | — |
| I23 | 90 | 52 | 8 |
| I24 | 120 | 49 | 12 |
| I25 | 180 | 47 | 9 |
| I26 | 240 | 43 | 20 |
| I27 | 300 | 35 | 27 |

[1]The percentages are based on the crude yield of nitrosocyclohexane or of cyclohexanone oxime based on tert-butyl nitrite Example I28

A second mixture consisting of tert-butyl nitrite (90% by weight in tert-butanol, Sigma-Aldrich; 0.5 mmol, 66 µl), cyclododecane (10 mmol; 1683 mg) and 1 ml of benzene was illuminated in a closed borosilicate tube at room temperature (29° C.) while stirring for 16 hours. Illumination was effected using a light-emitting diode (Nichia SMD LED UV NVSU233a) which emits light having a wavelength of 365 nm and has light intensity 1 W at 3.7 V and 1 A, applied to an aluminum heatsink. This formed the first product mixture. Nitrosocyclododecane and dodecanone oxime were determined in the first product mixture formed as described for nitrosocyclohexane and cyclohexanone oxime in examples 11 to 16 by means of $^1$H NMR spectroscopy. 46% crude yield of nitrocyclododecane based on tert-butyl nitrite was achieved.

Example I29

A second mixture consisting of tert-butyl nitrite (90% by weight in tert-butanol, Sigma-Aldrich; 0.5 mmol, 66 µl) and cyclopentane (10 mmol; 933 µl) was illuminated in a closed borosilicate tube at room temperature (20° C.) while stirring for 16 hours to obtain the first product mixture. Illumination was effected using a light-emitting diode (Nichia SMD LED UV NVSU233a) which emits light having a wavelength of 365 nm and has light intensity 1 W at 3.7 V and 1 A, applied to an aluminum heatsink. The determination of nitrosocyclopentane and cyclopentanone oxime in the first product mixture formed was effected by means of $^1$H NMR spectroscopy as described in examples B1 to B6 for nitrosocyclohexane and cyclohexanone oxime. A crude yield of cyclopentanone oxime of 61% based on tert-butyl nitrite was achieved.

Comparative Examples $C_{30}$ to $C_{37}$

A second mixture consisting of tert-butyl nitrite (90% by weight in tert-butanol; Sigma-Aldrich) and cyclohexane (Sigma-Aldrich) in the molar ratios specified in table 4 was illuminated in a quartz tube (for examples $C_{30}$ to $C_{33}$ a tube having a diameter of 10 mm was used, and for examples $C_{34}$ to $C_{37}$ a tube having a diameter of 6 mm) with a mercury vapor lamp (Normac UV-lamps TQ150 Z2; 200 nm) at room temperature (20° C.) while stirring. This formed the first product mixture. The determination of nitrosocyclohexane and cyclohexanone oxime in the first product mixture formed was effected after one hour and after four hours of illumination by means of $^1$H NMR spectroscopy as described in examples I1 to I6.

The results are shown in table 4.

TABLE 4

| Example | tert-Butyl nitrite [mmol] | Cyclohexane [mmol] | Nitrosocyclohexane [%] | | Cyclohexanone oxime [%][1] | |
|---|---|---|---|---|---|---|
| | | | after 1 h | after 4 h | after 1 h | after 4 h |
| C30 | 0.10 | 10 | 30 | 0 | 0 | 8 |
| C31 | 0.13 | 10 | 30 | 18 | 0 | 12 |
| C32 | 0.20 | 10 | 35 | 20 | 0 | 14 |
| C33 | 0.50 | 10 | 10 | 29 | 0 | 2 |
| C34 | 0.10 | 10 | 0 | 0 | 0 | 19 |
| C35 | 0.13 | 10 | 0 | 0 | 0 | 33 |
| C36 | 0.20 | 10 | 5 | 0 | 0 | 20 |
| C37 | 0.50 | 10 | 23 | 7 | 2 | 20 |

[1]The percentages are based on the crude yield of nitrosocyclohexane or of cyclohexanone oxime based on tert-butyl nitrite Comparative Example C38

A second mixture consisting of 188.4 g (2.239 mol) of cyclohexane and 11.6 g (112.5 mmol) of tert-butyl nitrite was pumped through a Teflon hose having a length of 3.8 m and an internal diameter 2 mm, which was wound around a cooling quartz tube of a mercury vapor lamp (150 W; TQ150, undoped). During that time, the second mixture was illuminated with the mercury vapor lamp. The composition of the first product mixture obtained was determined by means of quantitative HPLC by the method below. Table 5 reports the composition of the first product mixture obtained as a function of the residence time of the second mixture in the Teflon hose.

For the quantitative HPLC determination, an Agilent Series 1100 was used. The column used was a Zorbax Eclipse XDB-C18 1.8 µm 50*4.6 mm from Agilent. A UV detector (A=195 nm, BW=5 nm) was used; the flow rate was 1.3 ml/min, the injection was 5 µl, at a temperature of 20° C., a run time of 10 min and a pressure of about 250 bar. The eluent used was water with 0.1% by volume of $H_3PO_4$ or acetonitrile with 0.1% by volume of $H_3PO_4$. Calibration was effected with an external standard, with dissolution of the samples in an acetonitrile/water mixture (50% by volume/50% by volume). The first product mixture was likewise dissolved in this acetonitrile/water mixture. The spectrum obtained was evaluated by methods known to those skilled in the art.

TABLE 5

| Run | Residence time [min] | t-Butyl nitrite [mmol] | Cyclohexanone oxime [mmol] | Dimer[1] [mmol]* | Isomer of the dimer[2] [mmol]* | Yield [%] |
|---|---|---|---|---|---|---|
| 1 | 0.00 | 92.2 | 0.0 | 0.6 | 0.0 | 1 |
| 2 | 2.64 | 52.1 | 0.6 | 6.4 | 3.5 | 11 |
| 3 | 3.97 | 44.4 | 2.3 | 6.7 | 4.9 | 15 |
| 4 | 5.95 | 27.2 | 3.7 | 8.6 | 6.0 | 20 |
| 5 | 11.90 | 5.3 | 5.7 | 7.8 | 8.7 | 24 |

*calculated as monomer

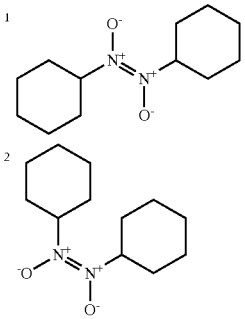

Comparative Example C39

A second mixture consisting of 376.8 g (4.477 mol) of cyclohexane and 23.2 g (225 mmol) of tert-butyl nitrite was pumped through a Teflon hose (length 3.8 m; internal diameter 2 mm; residence time 5.95 min.) which was wound around a cooling borosilicate tube of a mercury vapor lamp (150 W; TQ150, undoped). During that time, the second mixture was illuminated with the mercury vapor lamp. After illumination, cyclohexane and residual tert-butyl nitrite were evaporated and 24 g of n-hexane were added. The suspension was cooled to 0° C., filtered and washed with 10 ml of n-hexane at 0° C. 1.95 g (8.6 mmol) of the dimer were obtained.

Example I40

A sample of a second mixture consisting of 188.4 g (2.24 mol) of cyclohexane and 11.6 g (11.2 mmol) of tert-butyl nitrite were introduced into a cuvette (38×138×5 mm) and illuminated with 10 diodes which emit light having a wavelength of 365 nm. Table 6 reports the composition of the first product mixture obtained as a function of the reaction time (illumination time), with determination of the composition of the first product mixture by means of quantitative HPLC as described above in example 138.

TABLE 6

| Reaction time [min] | t-Butyl nitrite [mmol] | Cyclohexanone oxime [mmol] | Dimer[1] [mmol]* | Isomer of the dimer[2] [mmol]* | Yield [%] |
|---|---|---|---|---|---|
| 0 | 8.07 | 0.00 | 0.00 | 0.00 | 0 |
| 15 | 5.42 | 1.61 | 0.44 | 0.00 | 22.7 |
| 30 | 2.86 | 3.24 | 0.73 | 0.02 | 44.7 |
| 45 | 0.80 | 4.41 | 0.87 | 0.03 | 60.6 |
| 60 | 0.00 | 4.63 | 1.14 | 0.05 | 67.3 |

*calculated as monomer

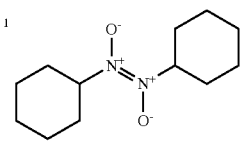

TABLE 6-continued

| Reaction time [min] | t-Butyl nitrite [mmol] | Cyclohexanone oxime [mmol] | Dimer[1] [mmol]* | Isomer of the dimer[2] [mmol]* | Yield [%] |
|---|---|---|---|---|---|

2

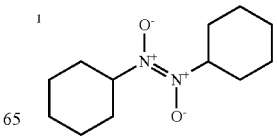

Example I41

A second mixture consisting of 568 g (6.75 mol) of cyclohexane and 34.8 g (337.5 mmol) of tert-butyl nitrite was pumped through a cuvette (38×138×5 mm), with a residence time of the second mixture in the cuvette of 5.95 min, during which the second mixture was illuminated with 10 diodes which emit light having a wavelength of 365 nm. After the illumination, cyclohexane and tert-butyl nitrite were evaporated at a maximum of 40° C. and there were two cycles of addition of 20 g of n-hexane and re-evaporation. The residue was suspended in 30 g of hexane. The suspension cooled to 0° C., filtered and washed with 10 ml of n-hexane. 10.2 g (45 mmol, 13%) of dimer were obtained.

Examples I42 and I43

A second mixture consisting of the components specified in table 7 in the molar ratios specified in table 7 was introduced into a cuvette (38×138×5 mm) and illuminated with 10 diodes which emit light having a wavelength of 365 nm for the period of time specified in table 7. The composition of the first product mixture which forms was determined by means of quantitative HPLC as described above in example 138. Table 7 shows the results.

TABLE 7

|  | I42 | I43 |
|---|---|---|
| Molar cyclohexane:tert-butyl nitrite:tert-butanol ratio | 20:1:8 | 20:1:0 |
| tert-Butyl nitrite [mmol] | 6.89 | 9.21 |
| Illumination time [min] | 45 | 60 |
| First product mixture (P1) |  |  |
| tert-Butyl nitrite [mmol] | 0.1 | 0 |
| Dimer[1] [mmol]* | 2.93 | 4.63 |
| Isomer of the dimer[2] [mmol]* | 0.77 | 1.14 |
| Cyclohexanone oxime [%] | 0.93 | 0.43 |
| Yield[3] [%] | 67.2 | 67.3 |
| Yield[4] [%] | 68.2 | 67.3 |

*calculated as monomer

TABLE 7-continued

|  | I42 | I43 |
|---|---|---|

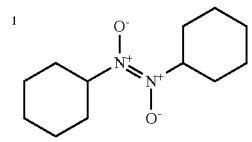

[3] based on tert-butyl nitrite used
[4] based on tert-butyl nitrite converted

Examples I44 and I45

A second mixture consisting of cyclohexane and tert-butyl nitrite in a molar ratio of 20:1 was introduced into a cuvette (38×138×5 mm) and illuminated with the number of diodes specified in table 8 and with the illumination time specified in table 8. The composition of the first product mixture formed was determined by means of quantitative HPLC as described in example 138. The results can be seen in table 8.

TABLE 8

|  | I44 | I45 |
|---|---|---|
| Number of diodes | 5 | 10 |
| Illumination time [min] | 90 | 45 |
| Stirring | yes | no |
| First product mixture (P1) |  |  |
| tert-Butyl nitrite [mmol] | 1.74 | 1.22 |
| Dimer[1] [mmol] | 6.62 | 6.72 |
| Isomer of the dimer[2] [mmol]* | 1.19 | 1.33 |
| Cyclohexanone oxime [%] | 0.44 | 0.47 |
| Yield[3] [%] | 58.9 | 60.8 |
| Yield[4] [%] | 67.3 | 66.6 |

*calculated as monomer

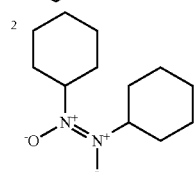

[3] based on tert-butyl nitrite used
[4] based on tert-butyl nitrite converted

The invention claimed is:

1. A process for preparing $C_4$-$C_{15}$ lactams, comprising the steps of:
   a) converting a first mixture (M1) comprising a $C_1$-$C_{10}$ alcohol, nitrogen oxides and oxygen to obtain a $C_1$-$C_{10}$-alkyl nitrite,
   b) converting a second mixture (M2) comprising the $C_1$-$C_{10}$-alkyl nitrite obtained in step a) and a $C_4$-$C_{15}$-cycloalkane to obtain a first product mixture (P1) comprising a $C_4$-$C_{15}$-nitrosocycloalkane, a dimeric $C_4$-$C_{15}$-nitrosocycloalkane, a $C_4$-$C_{15}$-cycloalkanone oxime and a $C_1$-$C_{10}$ alcohol,
   wherein the second mixture (M2) is illuminated during the conversion with a light-emitting diode that emits light having a wavelength in the range from 300 to 500 nm,
   c) preparing the $C_4$-$C_{15}$ lactam by conversion of the $C_4$-$C_{15}$-cycloalkanone oxime obtained in step b) in the presence of a catalyst by one of the following steps:
      c1) separating the $C_1$-$C_{10}$ alcohol from the first product mixture (P1) obtained in step b) to obtain a second product mixture (P2) comprising the $C_4$-$C_{15}$-cycloalkanone oxime,
         recycling the $C_1$-$C_{10}$ alcohol removed into the first mixture (M1) in step a) and
         converting the $C_4$-$C_{15}$-cycloalkanone oxime present in the second product mixture (P2) in the presence of the catalyst to obtain the $C_4$-$C_{15}$ lactam,
      or
      c2) converting the $C_1$-$C_{15}$-cycloalkanone oxime present in the first product mixture (P1) in the presence of the catalyst to obtain a third product mixture (P3) comprising the $C_4$-$C_{15}$ lactam and the $C_1$-$C_{10}$ alcohol,
         removing the $C_1$-$C_{10}$ alcohol present in the third product mixture (P3) to obtain the $C_4$-$C_{15}$ lactam and
         recycling the $C_1$-$C_{10}$ alcohol removed into the first mixture (M1) in step a).

2. The process according to claim 1, wherein the light-emitting diode in step b) emits light having a wavelength in the range from 340 to 390 nm.

3. The process according to claim 1, wherein the conversion of the first mixture (M1) in step a) is conducted at a temperature in the range from 10 to 300° C.

4. The process according to claim 1, wherein the conversion of the first mixture (M1) in step a) is conducted at a pressure in the range from 1 to 50 bar.

5. The process according to claim 1, wherein the conversion of the second mixture (M2) in step b) is conducted at a temperature in the range from −30 to 150° C.

6. The process according to claim 1, wherein the conversion of the second mixture (M2) in step b) is conducted at a pressure in the range from 1 to 10 bar.

7. The process according to claim 1, wherein the catalyst in step c) is selected from the group consisting of zeolites and inorganic acids.

8. The process according to claim 1, wherein the $C_4$-$C_{15}$-cycloalkanone oxime is in gaseous form during the conversion of the $C_4$-$C_{15}$-cycloalkanone oxime in step c).

9. The process according to claim 1, wherein the conversion of the $C_4$-$C_{15}$-cycloalkanone oxime in step c) is conducted at a temperature in the range from 50 to 500° C.

10. The process according to claim 1, wherein the conversion of the $C_4$-$C_{15}$-cycloalkanone oxime in step c) is conducted at a pressure in the range from 0.05 to 10 bar.

11. The process according to claim 1, wherein the $C_4$-$C_{15}$-cycloalkane in step b) is selected from the group consisting of cyclopentane, cyclohexane and cyclododecane.

12. The process according to claim 1, wherein the $C_1$-$C_{10}$ alcohol present in the first mixture (M1) in step a) is selected from the group consisting of methanol, tert-butanol and neopentanol.

* * * * *